United States Patent [19]

Sayer

[11] Patent Number: 4,876,206

[45] Date of Patent: Oct. 24, 1989

[54] METHODS FOR DETECTING RARE EARTH MINERALS

[76] Inventor: Wayne L. Sayer, 4213 Canal Cir., Las Vegas, Nev. 89122

[21] Appl. No.: 309,422

[22] Filed: Feb. 10, 1989

[51] Int. Cl.$^4$ ............................................. G01N 33/20
[52] U.S. Cl. ...................................... 436/82; 250/302; 250/461.1; 436/51; 436/172
[58] Field of Search .................................. 436/81–82, 436/172; 250/253, 302, 461

[56] References Cited

U.S. PATENT DOCUMENTS

| | | | |
|---|---|---|---|
| 3,484,380 | 12/1969 | Kleinerman | 250/459.1 |
| 3,539,941 | 11/1970 | Halverson | 372/52 |
| 3,793,527 | 2/1974 | Forest | 250/459.1 |
| 3,936,633 | 2/1976 | De Kalb et al. | 378/45 |
| 4,007,009 | 2/1977 | Wright | 436/103 |
| 4,724,217 | 2/1988 | Miller | 436/82 |
| 4,759,033 | 7/1988 | Ariessohn | 374/161 |

FOREIGN PATENT DOCUMENTS 0856988 12/1979 U.S.S.R. ................................ 436/82

OTHER PUBLICATIONS

Adams, J. W., et al, "Bibliography of the Geology and Mineralogy of the Rare Earths and Scandium to 1971", Geological Survey Bulletin 1366 (1973).
Anstett, T. F., "Availability of Rare-Earth, Yttrium, and Related Thorium Oxides–" Market Economy Countries-A Minerals Availability Appraisal, Library of Congress TN-295 U4.
Cava, R. J., et al., "Superconductivity Near 70K in a New Family of Layered Copper Oxides", Nature, vol. 336 (Nov. 17, 1988), pp 211–214.
Fleischer, M., Glossary of Mineral Species (1983).
Nichols, G. L., et al., "Rare Earths as Activators of Luminescence," J.O.S.A. & R.S.I. (Nov. 13, 1926), pp. 573–587.
Przibram, Dr. Karl, "Irradiation Colors and Luminescence-A Contribution to Mineral Physics," London, 1956.
Radley, J. A. et al., "Fluorescence Analysis in Ultraviolet Light," London, 1954.
Smith, Orsino C., "Identification and Qualitative Chemical Analysis of Minerals".
Guilbault, G., Practical Fluorescence, Theory, Methods, and Techiques, (New York), 1973.
Heylmun, E. B., "Rare Earth Placers", California Mining Journal (Aug. 1988), pp. 28–31.
Jacobson, Ralph E., The Manual of Photography (1978), pp. 400–401.
Molycorp., Inc., "Mountain Pass Operations".
Nature, vol. 134, No. 3351, Jan. 20, 1934, pp. 99–100.
Nature, vol. 133, No. 3364, Apr. 21, 1934, p. 623.
Nature, vol. 133, No. 3367, May 12, 1934, p. 736.
Nature, vol. 135, No. 3408, Feb. 23, 1935, p. 319.
Nature, vol. 135, No. 3403, Jan. 19, 1935, pp. 110, 100 ("Supplement to Nature").
Nature vol. 135, No. 3416, Apr. 27, 1935, p. 668.
Nature, vol. 135, No. 3420, May 18, 1935, p. 848.
Nature, vol. 139, No. 3512, Feb. 20, 1937, p. 329.
Nature, Mar. 20, 1937, p. 523, vol. 139, No. 3516.
Nature, Jun. 18, 1938, vol. 141, No. 3581, pp. 1113.

*Primary Examiner*—Robert J. Hill, Jr.
*Assistant Examiner*—Amalia L. Santiago
*Attorney, Agent, or Firm*—Workman, Nydegger & Jensen

[57] ABSTRACT

This invention relates to methods for quickly and accurately detecting the presence of rare earth minerals which can be performed in the field. An ore sample to be tested for the presence of rare earth minerals is contacted with both a basic reagent, preferably containing an alkali metal, and with a halide acid such as hydrochloric acid. Once the treated ore sample is dry, it is examined under a shortwave ultraviolet light for fluorescence of a red-orange color. If rare earth minerals are present, fluorescence of a red-orange color will occur. If no rare earth minerals are present, no red-orange fluorescence is observed. The sensitivity of the disclosed methods to rare earth minerals may be varied by altering the basic reagent to permit the user to "zero in" on the most concentrated source of rare earth minerals.

51 Claims, No Drawings

METHODS FOR DETECTING RARE EARTH MINERALS

BACKGROUND

1. The Field of the Invention

The invention relates to methods for detecting rare earth minerals. More particularly, the present invention provides quick and accurate methods for detecting the presence of rare earth minerals which can be performed in the field.

2. Technology Review

The rare earth elements, or lanthanides, are the fifteen elements in the periodic table from atomic number 57 through 71. Although not members of the lanthanide series, yttrium (atomic number 39) and scandium (atomic number 21) are often grouped with the rare earth elements because they frequently occur with them in nature and have similar chemical properties.

As a group, the rare earth elements are more abundant in the earth's crust than nickel or copper; cerium alone is more abundant than tin; neodymium and lanthanum are more abundant than lead. Although elements of the lanthanide series are historically called "rare earths", they are neither rare nor earths ("earths" being a term used for oxides in the century of early lanthanide discovery).

One of the most important applications of rare earths is in catalytic activities. Petroleum refineries use a lanthanum-rich rare earth mixture to increase the yield of gasoline and other aromatics from heavy crude oils.

Another significant application of rare earths is in the field of high temperature superconductors. Certain lanthanum- and yttrium-containing compounds are known to possess high temperature superconducting properties. In addition, many other rare earth-containing compounds are being examined for high temperature super conductivity.

Mischmetal, produced by the electrolysis of anhydrous mixed rare earth chlorides, has applications in the iron and steel and the cigarette lighter flint industries. In the iron and steel industry, the physical and rolling properties of the metal are improved by the use of mischmetal. Rare earth treated, high strength, low alloy steels are being increasingly used in the automobile industry as structural components and in lightweight steel applications.

Rare earth metals are used in the manufacture of permanent magnets. These high strength permanent magnets result in lighter, smaller, and more energy efficient electric motors and generators.

The red phosphor component in all color television sets uses europium and yttrium oxides. In addition, color television face plates contain neodymium to enhance the picture brightness and contrast. X-ray intensification screens containing lanthanum or gadolinium based phosphors reduce patient diagnostic exposure times by more than half.

Other important applications of the rare earths include: ceramics and optics (including polishing compounds and glass additives), electronics, nuclear energy, lighting and lasers. New uses for rare earth minerals in high technology industries are being discovered every year.

The rare earth elements and yttrium are essential constituents in more than 100 rare earth minerals. However, only a few rare earth minerals occur in sufficient concentration to qualify as ore. Monazite, bastnasite, xenotime, euxenite, samarskite, and allanite are a few examples of the many rare earth minerals. Of these rare earth minerals, bastnasite is of particular importance in the United States. The world's largest producer of bastnasite is the mine at Mountain Pass, Calif. Although rare earth elements are not as rare as once believed, minable deposits of rare earth minerals are rare.

Identification of rare earth elements is difficult, and identification of rare earth minerals is also difficult. One explanation for the difficulty of chemically identifying rare earths lies in the fact that virtually all of the rare earth elements are characterized by a +3 oxidation state. The lanthanides are characterized by the gradual filling of the $4f$ subshell. The relative energies of the $5d$ and the $4f$ orbitals are very similar and sensitive to the occupancy of these orbitals. The universal preference for the +3 oxidation state together with the notable similarity in size led to great difficulties in separating rare earth elements prior to the development of chromatographic methods.

In addition, as a consequence of the poor shielding of the $4f$ electrons, there is a steady increase in effective nuclear charge and concomitant reduction in size. The ionic radius of the trivalent ion from lanthanum to lutetium gradually decreases in size, an effect known as the lanthanide contraction. As a result, the heavier rare earth elements have an ionic radius similar to much lighter elements, such as yttrium.

Since rare earth minerals are not readily identifiable, especially if they are not radioactive, it is fairly likely that commercially important deposits of rare earth minerals exist in many parts of the nation. Of the thirty important rare earth minerals, only half are radioactive. However, they are usually associated with minerals which are radioactive, so radioactivity is an important feature in identifying rare earth minerals. Radioactivity may aid in the discovery of rare earth deposits, but it is also an expensive nuisance, as safeguards must be taken and regulatory standards maintained while handling concentrates.

Rare earth minerals are often found disseminated in potash-rich igneous rocks, and they are commonly in complex pegmatite dikes along with many other rare minerals and gemstones. Rare earth minerals like bastnasite are occasionally found in large quantities in an unusual marble-like intrusive igneous rock known as "carbonatite." Sometimes, rare earth minerals are found disseminated in metamorphic rocks such as gneiss and schist. They are also found in certain veins and along fault zones in association with hematite, barite, fluorite, and other minerals. The presence of smoke quartz and radioactive halos is sometimes a clue to rare earths, since they are usually associated with radioactive minerals if they are not radioactive themselves. Thus, the principal tool used in prospecting for rare earths is a radiation detector such as a geiger counter or scintillometer. Airborne radiometric surveys are also useful in finding larger placer deposits.

As mentioned above, rare earth minerals are difficult to identify. Most rare earth minerals are undifferentiated and distinguishable to only the most sophisticated mineralogist in the field. Radioactivity of many rare earth minerals is a useful aid in identifying the possible presence of rare earth minerals. However, the radioactivity of an ore sample provides the prospector with no specific information concerning whether the sample is a radioactive rare earth mineral or some other radioactive mineral. The actinides, as well as many other elements which are not rare earths, are also radioactive. Thus, even if an ore sample is radioactive, it is still necessary to have that sample analyzed to determine whether it contains rare earth elements.

Currently, the only known method for accurately detecting rare earth minerals is to have the ore sample analyzed in a laboratory. These laboratory procedures generally are used to identify the presence of specific rare earth elements. Such procedures are sophisticated and require expensive equipment to perform x-ray diffraction, x-ray optical fluorescence, atomic absorption or other chemical or spectroscopic analysis of the sample.

Neither spectroscopic nor x-ray analysis procedures for detecting rare earth minerals can presently be conveniently carried out in the field. Similarly, chemical analysis cannot be conveniently performed in the field without somewhat complicated equipment and burdensome processes. Thus, none of the current methods for detecting rare earth elements can be conveniently adapted for routine analysis or assay of rare earth mineral samples in the field.

In summary, rare earth elements obtained from rare earth minerals are playing an increasingly important role in today's society. The sophisticated and complex analytical techniques for identifying the presence of rare earth elements may not be suitably adapted for detecting the presence of rare earth minerals in the field. It will be appreciated that it would be a significant advancement in the art to provide methods for detecting rare earth minerals which can be performed in the field.

Additionally, it would be a significant advancement in the art to provide methods for detecting rare earth minerals which provide quick and accurate results.

It would be another advancement in the art to provide methods for detecting rare earth minerals which do not require sophisticated chemicals, processes, or equipment.

It would be a further advancement in the art to provide methods for detecting rare earth minerals which use relatively safe and self-neutralizing reagents.

It would be yet another advancement in the art to provide methods for detecting rare earth minerals which do not require the use of radioactivity detectors.

Such methods for detecting rare earth minerals are disclosed and claimed herein.

BRIEF SUMMARY AND OBJECTS OF THE INVENTION

The present invention is directed to methods for detecting rare earth minerals in the field. One preferred method for detecting rare earth minerals involves mixing an ore sample with dry, granular basic reagent, such as sodium hydroxide. Preferably, approximately equal volumes of ore sample and basic reagent are mixed.

Next, the mixture of ore sample and basic reagent is preferably treated with a halide acid, such as hydrochloric acid, and allowed to react, cool off, and dry. Approximately one to three volume measures of acid are preferably applied to the mixture. Once the sample is dry, it is examined under a shortwave ultraviolet light for fluorescence of a red-orange color. If rare earth minerals are present, fluorescence of a red-orange color will occur. If no rare earth minerals are present, the reactant will not fluoresce red-orange, or any other color.

The basic reagent mixed with the ore sample may vary depending upon the desired sensitivity of the test. For example, for very high sensitivity, sodium carbonate ("soda ash") is preferably used. For a moderately sensitive test, trisodium phosphate ("TSP"), sodium chlorite ($NaClO_2$), sodium sulfite ($Na_2SO_3$) or potassium peroxymonosulfate may be used. For a low sensitivity test, sodium hydroxide ("lye"), or sodium bicarbonate ("baking soda") may be used.

In addition, the basic reagent may be in a liquid form. For example, satisfactory results have been obtained by treating the ore sample with ordinary swimming pool chlorine (sodium hypochlorite, NaOCl, 10% solution) saturated with sodium chloride at 100° F. and hydrochloric acid, all in approximately equal volume. Drying time is longer, but remarkably bright red-orange fluorescence results. Similarly, aqueous solutions of trisodium phosphate, sodium carbonate, sodium sulfite, sodium chlorite, and sodium hydroxide have provided satisfactory results.

The use of all-liquid reagents permits true in situ testing. Rock or sand can be tested for the presence of rare earth minerals by applying the acid and base directly onto the rock or sand surface. After reacting and drying, the rock or sand is examined under a shortwave utlraviolet light for fluorescence of a red-orange color, as discussed above.

The above methods are quick, inexpensive, very specific, and dramatic in results. The equipment is relatively inexpensive, simple, easy to carry, and rapidly deployed. The chemicals used are common household and swimming pool items which are relatively safe to use and self-neutralizing. The results are easy to interpret, reproducible, stable, easily recorded, and storable.

A significant advantage of the methods of detecting rare earth minerals within the scope of the present invention is the ease and speed with which a definitive test for the rare earth minerals can be carried out directly in the field. Within a matter of minutes the prospector can test an ore sample and accurately determine whether rare earth minerals are present. Depending on the basic reagent which was initially mixed with the ore sample, the prospector can further obtain accurate information about the relative concentrations of rare earth minerals.

Thus, exciting possibilities for new discoveries of rare earth minerals are now possible using the methods of the present invention. It is now possible to quickly and accurately sample and test alluvial fans for upstream rare earth mineral deposits, much like the old-timers prospected for gold by following "colors" in the pan to their upstream or uphill origins.

It is, therefore, an object of the present invention to provide methods for detecting rare earth minerals which can be carried out directly in the field.

Another important object of the present invention is to provide methods for detecting rare earth minerals which provide quick and accurate results.

An additional important object of the present invention is to provide methods for detecting rare earth minerals which do not require sophisticated chemicals, processes, or equipment.

Still another important object of the present invention is to provide methods for detecting rare earth minerals which use relatively safe and self-neutralizing reagents.

A further object of the present invention is to provide methods for detecting rare earth minerals which do not require radioactivity detectors.

Another important object of the present invention is to provide methods for detecting rare earth minerals which provide accurate semi-quantitative results.

These and other objects and features of the present invention will become more fully apparent from the following description and appended claims or may be learned from the practice of the invention.

DETAILED DESCRIPTION OF THE PREFERRED EMBODIMENTS

The present invention relates to methods for detecting rare earth minerals which can be conveniently carried out in the field. The general method for detecting rare earth minerals involves mixing one volume measure of ore sample with an approximately equal volume measure of a dry, granular basic reagent. The dry mixture is preferably placed in an inert absorbent test receptacle, such as an ordinary paper cup, coffee filter, or other similar container.

The mixture of ore sample and basic reagent is then preferably treated with approximately one to three volume measures of a halide acid, such as hydrochloric acid, and allowed to react, cool off, and dry. Once the sample is dry, it is examined under a shortwave ultraviolet light for fluorescence of a red-orange color. The drying process is very important. Noticeably damp or wet reactant will not fluoresce. If rare earth minerals are present, the sample will fluoresce with a striking red-orange upon the drying crystals which form upon the outer surface of the sample. If no rare earth minerals are present, the reactant will not fluoresce red-orange, or any other color.

The ore sample to be tested for the presence of rare earth minerals preferably has a sample size less than about one-quarter ($\frac{1}{4}$) inch in diameter. The quantity of ore sample required preferably is in the range from about a quarter ($\frac{1}{4}$) teaspoon of ore to about two tablespoons of ore.

Larger quantities of ore sample could also be tested using the methods of the present invention; however, the larger the quantity of ore sample the larger the quantities of acid and base needed to react with the ore. When the acid is added to the solid granular mixture of ore and base, a fuming and sputtering reaction results. This reaction proceeds after all of the liquid acid is added, generating a considerable amount of heat. Therefore, it is preferable to limit the volume of the ore sample due to the buildup of heat and pressure as the reaction proceeds.

If the mineral ore sample size exceeds about one-quarter ($\frac{1}{4}$) inch, then the sample can be conveniently ground in a mortar to a size below one-quarter ($\frac{1}{4}$) inch. However, usually a sufficient quantity of ore sample may be obtained using a simple garden trowel and removing by hand any larger rocks.

The basic reagent, which is mixed with the ore sample, may vary depending upon the desired sensitivity of the test. For a very high sensitivity (one part in 100,000), sodium carbonate ("soda ash") may be used preferably used. For a moderately sensitive (one part in 10,000) test, trisodium phosphate ("TSP"), sodium chlorite ($NaClO_2$), sodium sulfite ($Na_2SO_3$), potassium peroxymonosulfate, or sodium hypochlorite ($NaOCl$) in a 10% solution saturated with ordinary table salt may be preferably used as the basic reagent. For a low sensitivity (one part in 1,000), semi-quantitative test, sodium hydroxide ("lye") or sodium bicarbonate may preferably be used.

When using dry, granular basic reagents, it has been found that mixing approximately equal volumes of the basic reagent with the ore sample produces acceptable results. Of course the required amount of basic reagent may vary depending on the concentration or purity of the basic reagent. For example, a smaller quantity of a very pure basic reagent will usually result in the same result as a larger quantity of less pure basic reagent. As a result, it is not necessary to use "reagent grade" or very pure basic reagents, for the same results may be achieved with less expensive "technical grade" reagents.

An important feature of the present invention is the ability to detect rare earth minerals in the field. Thus, the methods within the scope of the present invention are not intended to be performed with strict accuracy. The methods may be performed by a person in the field who does not always measure and mix exactly equal quantities of reagents. Hence, slight variations in the quantity of reagents added do not significantly affect the ultimate result.

As discussed above, after the basic reagent is mixed with the ore sample and placed within the test receptacle, the solid granular mixture of ore and base is preferably treated with hydrochloric acid. The acid is preferably carefully added to the mixture to minimize the fuming and sputtering which occurs upon the direct addition of acid with a base. The mixture is preferably allowed to cool off to ambient temperature before further handling is attempted.

Other halide acids such as hydroiodic acid, hydrobromic acid, and hydrofluoric acid could also be suitably used in the methods of the present invention. However, their highly corrosive nature together with their limited availability and high cost make them less desirable than hydrochloric acid. Hydrochloric acid is presently preferred because of its availability and low cost. It is not necessary to use high purity or reagent grade hydrochloric acid in the methods of the present invention. Ordinary hydrochloric acid (technical grade), such as that sold by swimming pool supply stores or grocery stores under the name muriatic acid, will produce suitable results.

Other inorganic acids such as sulfuric acid and nitric acid have failed to produce acceptable results when used with calcium-containing basic reagents, such as calcium chloride and calcium hypochlorite. As a result, it is currently believed that the presence of halide ions is important to achieve suitable results.

After the test mixture has dried, it is examined under a shortwave ultraviolet light for fluorescence of a red-orange color. One suitable shortwave ultraviolet light source is identified by the trademark MINERA-LIGHT® manufactured by Ultra-Violet Products, Inc., San Gabriel, Calif. The light has a wavelength of 254 nanometers.

It is presently believed that the foregoing advantageous results of the invention are obtained because a halide salt of sodium is formed when the sodium in the basic reagent combines with the halide ions from the acid. If the mineral sample contains rare earth minerals, the methods of the present invention create a new alkali metal-halide salt which has been doped by the rare earth component of the mineral ore. The derived alkali metal salt is responsive to the shortwave ultraviolet hand-held light. Fluorescence only occurs under shortwave ultraviolet radiation if the alkali metal halide salt is sensitized by doping from the rare earth mineral. Longwave ultraviolet light will not bring on the fluorescence. If there are no rare earth minerals present in the sample, no fluorescence is observed.

It has been found that the dried test sample may be stored for at least ten months without losing the ability to fluoresce under a shortwave ultraviolet light. Thus, samples tested in the field may not only be recorded photographically, but may be stored for extended periods of time.

Another useful method for detecting rare earth minerals within the scope of the present invention involves contacting the ore sample with liquid acid and liquid base. The ore sample is allowed to dry and then examined under ultraviolet light as discussed above.

The use of all-liquid reagents permits rapid in situ testing of sand and rock samples. For example, a shallow furrow may be made in alluvial sand. The furrow bottom is wetted with acid and base, allowed to dry, and examined under an ultraviolet light. The furrow is preferably examined at night under the ultraviolet light, but day time examination may be performed if daylight is properly shielded. Upon observation, if an orange-red fluorescence appears in the bottom of the furrow, rare earth minerals are present. The foregoing procedure is fast and does not require sophisticated equipment. The results may be recorded photographically or electronically by suitable sensors and recorders.

Similarly, an actual rock face may be tested for the presence of rare earth minerals without the necessity of cutting a channel or notch in the rock or chipping off a sample for grinding. A few drops of hydrochloric acid may be applied to the rock in a sufficient amount such that the acid begins to run off the face of the rock formation. Thereafter a few drops of the desired liquid base may be quickly applied to the rock formation, taking care to apply the base such that it does not all run off the face of the rock. The rock surface is allowed to dry and examined under the short wave ultraviolet light. If the rock contains a rare-earth mineral it will fluorescence red-orange. Barren rock, such as quartz, shows up as a void in the flouorescence. Depending on the circumstances, it may be provident to clean the rock face so that contamination from soil and earth does not interfere with the process.

It has been found that the acid is preferably not diluted very much, if at all. Whereas, adding water to the base solution does not appear to diminish the intensity of the fluorescence so long as the sample is allowed to dry thoroughly. It is presently believed that too much undiluted acid can overwhelm the base, but copious amounts of diluted base does not overwhelm the acid as long as drying can occur.

In situ testing for rare earth minerals within the scope of the present invention is not limited to the use of all-liquid reagents. Dry basic reagent may be mixed with sand in a furrow bottom made in alluvial sand. Acid may then be poured onto the furrow bottom as discussed above. After drying, the treated furrow bottom is examined under an ultraviolet light for the presence of rare earth minerals.

In situ testing for the presence of rare earth minerals within the scope of the present invention may lend itself to automation. A machine is contemplated which could travel over the ground, take periodic ore samples and chemically treat the ore samples. The samples could be viewed en masse and several miles of land could be tested in one day. Similarly, a portable machine is contemplated which would automatically treat an ore sample placed therein with the proper chemical reagents. Such a machine would provide more uniform test results.

EXAMPLES

The use of the methods for detecting rare earth minerals within the scope of the present invention will be further clarified by a consideration of the following examples, which are intended to be purely exemplary of the use of the invention and should not be viewed as a limitation on any claimed embodiment.

EXAMPLE 1

A quantity of bastnasite ore was obtained from the mine at Mountain Pass, Calif. and tested for the presence of rare earth minerals. The bastnasite ore was coarse, having a particle sizes less than one quarter (¼) inch. The bastnasite ore was unmortared, unsifted mill run ore believed to contain a rare earth mineral content of six percent (6%) according to the mine manager.

According to the procedure of Example 1, one quarter (¼) teaspoon of the bastnasite ore was mixed with one quarter (¼) teaspoon of sodium hydroxide. The sodium hydroxide was in the form of ordinary household lye purchased at a local grocery store. The mixture of bastnasite ore and sodium hydroxide was placed in a disposable coffee filter.

One half (½) teaspoon of 31.4% hydrochloric acid was then gradually poured onto the mixture. The hydrochloric acid was technical grade hydrochloric acid purchased at a local pool supply store under the name muriatic acid.

The mixture fumed and sputtered evidencing a reaction between the sodium hydroxide and the hydrochloric acid. The mixture was thereafter allowed to cool and dry. Upon drying, the mixture was viewed under a shortwave ultraviolet light having a wavelength of 254 nanometers. The sample fluoresced a red-orange color indicating the presence of rare earth minerals.

EXAMPLE 2

A quantity of bastnasite ore was obtained from the mine at Mountain Pass, Calif. and tested for the presence of rare earth minerals according to the procedure of Example 1, except that sodium carbonate (also known as "soda ash") was mixed with the bastnasite ore instead of the sodium hydroxide.

Upon drying, the treated mixture was viewed under a shortwave ultraviolet light having a wavelength of 254 nanometers. The sample fluoresced a very bright red-orange color indicating that the basic reagent sodium carbonate produces acceptable results according to the procedures of the present invention.

EXAMPLE 3

A quantity of bastnasite ore was obtained from the mine at Mountain Pass, Calif. and tested for the presence of rare earth minerals according to the procedure of Example 1, except that trisodium phosphate (also known as "TSP") was mixed with the bastnasite ore instead of the sodium hydroxide.

Upon drying, the treated mixture was viewed under a shortwave ultraviolet light having a wavelength of 254 nanometers. The sample fluoresced a bright red-orange color indicating that the basic reagent trisodium phosphate produces acceptable results according to the procedures of the present invention.

EXAMPLE 4

A quantity of bastnasite ore was obtained from the mine at Mountain Pass, Calif. and tested for the presence of rare earth minerals according to the procedure of Example 1, except that calcium chloride was mixed with the bastnasite ore instead of the sodium hydroxide.

Upon drying, the treated mixture was viewed under a shortwave ultraviolet light having a wavelength of 254 nanometers. The sample did not fluoresce a red-orange color indicating that the basic reagent calcium chloride did not produce acceptable results.

EXAMPLE 5

A quantity of bastnasite ore was obtained from the mine at Mountain Pass, Calif. and tested for the presence of rare earth minerals according to the procedure of Example 1, except that calcium hypochloride was mixed with the bastnasite ore instead of the sodium hydroxide.

Upon drying, the treated mixture was viewed under a shortwave ultraviolet light having a wavelength of 254 nanometers. The sample did not fluoresce a red-orange color indicating that the basic reagent calcium hypochlorite did not produce acceptable results.

EXAMPLE 6

A quantity of bastnasite ore was obtained from the mine at Mountain Pass, Calif. and tested for the presence of rare earth minerals according to the procedure of Example 1, except that magnesium carbonate was mixed with the bastnasite ore instead of the sodium hydroxide.

Upon drying, the treated mixture was viewed under a shortwave ultraviolet light having a wavelength of 254 nanometers. The sample did not fluoresce a red-orange color indicating that the basic reagent magnesium carbonate did not produce acceptable results.

EXAMPLE 7

A quantity of bastnasite ore was obtained from the mine at Mountain Pass, Calif. and tested for the presence of rare earth minerals according to the procedure of Example 1, except that potassium carbonate was mixed with the bastansite ore instead of the sodium hydroxide.

Upon drying, the treated mixture was viewed under a shortwave ultraviolet light having a wavelength of 254 nanometers. The sample fluoresced a very faint red-orange color indicating that the basic reagent potassium carbonate might produce acceptable results in some limited circumstances.

EXAMPLE 8

A quantity of limestone was obtained and tested for the presence of rare earth minerals according to the procedure of Example 1. Upon drying, the treated mixture of limestone and sodium hydroxide was viewed under a shortwave ultraviolet light having a wavelength of 254 nanometers. The sample did not fluoresce a red-orange color indicating that the limestone did not contain rare earth minerals.

EXAMPLE 9

A quantity of sandstone was obtained and tested for the presence of rare earth minerals according to the procedure of Example 1. Upon drying, the treated mixture of sandstone and sodium hydroxide was viewed under a shortwave ultraviolet light having a wavelength of 254 nanometers. The sample did not fluoresce a red-orange color indicating that the sandstone did not contain rare earth minerals.

EXAMPLE 10

A quantity of silica sand was obtained and tested for the presence of rare earth minerals according to the procedure of Example 1. Upon drying, the treated mixture of silica sand and sodium hydroxide was viewed under a shortwave ultraviolet light having a wavelength of 254 nanometers. The sample did not fluoresce a red-orange color indicating that the silica sand did not contain rare earth minerals.

EXAMPLE 11

A quantity of commercial gravel was obtained and tested for the presence of rare earth minerals according to the procedure of Example 1. Upon drying, the treated mixture of commercial gravel and sodium hydroxide was viewed under a shortwave ultraviolet light having a wavelength of 254 nanometers. The sample did not fluoresce a red-orange color indicating that the commercial gravel did not contain rare earth minerals.

EXAMPLE 12

A quantity of copper ore was obtained from Pioche, Lincoln County, Nev., and tested for the presence of rare earth minerals according to the procedure of Example 1. Upon drying, the treated mixture of copper ore and sodium hydroxide was viewed under a shortwave ultraviolet light having a wavelength of 254 nanometers. The sample did not fluoresce a red-orange color indicating that the copper ore did not contain rare earth minerals.

EXAMPLE 13

A quantity of galena ore was obtained from the Fredrickson mine, Goodsprings, Nev., and tested for the presence of rare earth minerals according to the procedure of Example 1. Upon drying, the treated mixture of galena ore and sodium hydroxide was viewed under a shortwave ultraviolet light having a wavelength of 254 nanometers. The sample did not fluoresce a red-orange color indicating that the galena ore did not contain rare earth minerals.

EXAMPLE 14

A quantity of country rocks not known to contain rare earth minerals was obtained and tested for the presence of rare earth minerals according to the procedure of Example 1. Upon drying, the treated mixture of country rocks and sodium hydroxide was viewed under a shortwave ultraviolet light having a wavelength of 254 nanometers. The sample did not fluoresce a red-orange color indicating that the country rocks did not contain rare earth minerals.

EXAMPLE 15

A quantity of monazite ore, reputed to contain rare earth oxides based upon tests performed in Washington D.C. by the Bureau of Mines, was obtained and tested for the presence of rare earth minerals according to the procedure of Example 1. Upon drying, the treated mixture of monazite ore and sodium hydroxide was viewed under a shortwave ultraviolet light having a wavelength of 254 nanometers. The sample showed a good a red-orange fluorescence indicating that the monazite ore contained rare earth minerals.

EXAMPLE 16

A quantity of bastnasite was obtained from the mine at Mountain Pass, Calif. and tested for the presence of rare earth minerals according to the procedure of Example 1, except that sulfuric acid was used to treat the mixture of bastnasite ore and sodium hydroxide. Upon drying, the treated mixture was viewed under a shortwave ultraviolet light having a wavelength of 254 nanometers. The sample did not fluoresce a red-orange color indicating that the sulfuric acid did not produce acceptable results ultilizing the methods within the scope of the present invention.

EXAMPLE 17

A quantity of bastnasite was obtained from the mine at Mountain Pass, Calif. and tested for the presence of rare earth minerals according to the procedure of Example 1, except that nitric acid was used to treat the mixture of bastnasite ore and sodium hydroxide. Upon drying, the treated mixture was viewed under a shortwave ultraviolet light having a wavelength of 254 nanometers. The sample did not fluoresce a red-orange color indicating that the nitric acid did not produce acceptable results ultilizing the methods within the scope of the present invention.

As discussed above, an important feature of the present invention is that the basic reagent does not need to be granular, solid, or dry. Hydrous solutions work equally well, only they require additional time to dry or "develop" sufficiently to fluoresce under the ultraviolet light. Using all liquid reagents, additional experiments were performed to further clarify the acceptable parameters of the methods within the scope of the present invention.

EXAMPLE 18

A quantity of bastnasite ore was obtained from the mine at Mountain Pass, Calif. and tested for the presence of rare earth minerals. According to the procedure of Example 18, one quarter (¼) teaspoon of the bastnasite ore was mixed with one quarter (¼) teaspoon of aqueous sodium hypochlorite which had been saturated with ordinary table salt (sodium chloride) at 100° F. It is believed the sodium chloride enhances the effectiveness of the sodium hypochlorite.

The sodium hypochlorite was purchased in the form of ordinary swimming pool chlorine with NaOCl as the active ingredient in a 10% aqueous solution (CLOROX® has the same active ingredient (NaOCl) in a 5.24% aqueous solution). The bastnasite ore was coarse, having a particle sizes less than one quarter (¼) inch. The bastnasite ore was unmortared, unsifted mill run ore believed to contain a rare earth mineral content of six percent (6%).

The mixture of bastnasite ore and sodium hypochlorite was placed in a disposable coffee filter. One quarter (¼) teaspoon of 31.4% hydrochloric acid was gradually poured onto the mixture. The hydrochloric acid was technical grade hydrochloric acid purchased at a local pool supply store under the name muriatic acid. The mixture fumed and sputtered evidencing a reaction between the sodium hypochlorite and the hydrochloric acid. The mixture was thereafter allowed cool and dry. Upon drying, the treated mixture was viewed under a shortwave ultraviolet light having a wavelength of 254 nanometers. The sample fluoresced a bright red-orange color indicating the presence of rare earth minerals.

When aqueous sodium hypochlorite is used as the basic reagent, as in Example 18, the sodium hypochlorite preferably has a concentration in the range from about 5% to about 15%. Thus, CLOROX® which is a 5.24% aqueous solution of sodium hypochlorite, would be a suitable basic reagent.

EXAMPLE 19

A quantity of bastnasite ore was obtained from the mine at Mountain Pass, Calif. and tested for the presence of rare earth minerals. According to the procedure of Example 19, one quarter (¼) teaspoon of the bastnasite ore was mixed with one quarter (¼) teaspoon of aqueous sodium hypochlorite which had been saturated with ordinary table salt (sodium chloride) at 100° F. It is believed the sodium chloride enhances the effectiveness of the sodium hypochlorite.

The sodium hypochlorite was purchased in the form of ordinary swimming pool chlorine with NaOCl as the active ingredient in a 10% aqueous solution. The bastnasite ore was coarse, having a particle sizes less than one quarter (¼) inch. The bastnasite ore was unmortared, unsifted mill run ore believed to contain a rare earth mineral content of six percent (6%).

The mixture of bastnasite ore and sodium hypochlorite was placed in a disposable coffee filter and allowed to dry. Upon drying, the treated mixture was viewed under a shortwave ultraviolet light having a wavelength of 254 nanometers. The sample failed to fluoresce a red-orange (or any other) color indicating that treatment with acid is an important step in detecting the presence of rare earth minerals within the scope of the present invention.

EXAMPLE 20

A quantity of bastnasite ore was obtained from the mine at Mountain Pass, Calif. and tested for the presence of rare earth minerals. According to the procedure of Example 20, one quarter (¼) teaspoon of the bastnasite ore was mixed with one quarter (¼) teaspoon of hydrochloric acid was gradually poured onto the mixture. The hydrochloric acid was technical grade hydrochloric acid purchased at a local pool supply store under the name muriatic acid. The bastnasite ore was coarse, having a particle sizes less than one quarter (¼) inch. The bastnasite ore was unmortared, unsifted mill run ore believed to contain a rare earth mineral content of six percent (6%).

The mixture of bastnasite ore and muriatic acid was placed in a disposable coffee filter and allowed to dry. Upon drying, the treated mixture was viewed under a shortwave ultraviolet light having a wavelength of 254 nanometers. The sample failed to fluoresce a red-orange (or any other) color indicating that treatment with basic reagent, such as sodium hypochlorite, is an important step in detecting the presence of rare earth minerals within the scope of the present invention.

EXAMPLE 21

As a follow up to the results of Example 18, a quantity of bastnasite ore was obtained from the mine at Mountain Pass, Calif. and tested for the presence of rare earth minerals according to the procedure of Example 1, except that KODAK® "Hypo Clearing Agent"

(Cat. 1533942) was mixed with the bastnasite ore instead of the sodium hydroxide.

Upon drying, the treated mixture was viewed under a shortwave ultraviolet light having a wavelength of 254 nanometers. The sample fluoresced a bright red-orange color indicating that the KODAK ® "Hypo Clearing Agent" used as the basic reagent produced acceptable results in the methods within the scope of the present invention.

Based upon Ralph E. Jacobson, et al., *The Manual of Photography*, Focal Press, London, 7th ed., pg. 400–401, 1978, it is believed that KODAK ® "Hypo Clearing Agent" is sodium sulfite ($Na_2SO_3$). To confirm this proposition, a quantity of sodium sulfite was obtained and tested according to the procedure of Example 21. Virtually identical results were obtained using sodium sulfite instead of KODAK ® "Hypo Clearing Agent".

EXAMPLE 22

A quantity of bastnasite ore was obtained from the mine at Mountain Pass, Calif. and tested for the presence of rare earth minerals according to the procedure of Example 1, except that "Leslie's Chlor-brite" fast dissolving pool chlorine concentrate, active ingredient sodium dichloro-S-triazinetrione (99.5%), was mixed with the bastnasite ore instead of the sodium hydroxide.

Upon drying, the treated mixture was viewed under a shortwave ultraviolet light having a wavelength of 254 nanometers. The sample fluoresced a red-orange color, about the intensity of the fluorescence produced using sodium hydroxide, indicating that the sodium dichloro-S-triazinetrione used as the basic reagent produced acceptable results in the methods within the scope of the present invention.

EXAMPLE 23

Further experiments were performed to verify the sensitivity of the methods for detecting rare earth minerals within the scope of the present invention. Twenty (20) milligrams of 10% bastnasite ore were mixed with a 200 gram base matrix sample of pure white washed silica sand. The bastnasite ore was ground to 100 mesh. An equal volume of sodium carbonate was further mixed with the sand/bastnasite mixture. Two volumes of hydrochloric acid were added to the mixture according to the procedure described in Example 1.

Upon drying, the treated mixture was viewed under a shortwave ultraviolet light having a wavelength of 254 nanometers. The sample fluoresced a red-orange color indicating the presence of rare earth minerals. The foregoing procedure results in a sensitivity to rare earth minerals of 1:100,000. (20 mg. of 10% bastnasite ore:200,000 mg. sand).

Parallel negative tests with a blank sand sample containing no bastnasite ore demonstrated that no rare earth minerals were included in the test materials.

EXAMPLE 24

Two hundred (200) milligrams of 10% bastnasite ore were mixed with a 200 gram base matrix sample of pure white washed silica sand, according to the procedure of Example 23 except that an equal volume of trisodium phosphate was further mixed with the sand/bastnasite mixture instead of sodium carbonate. Two volumes of hydrochloric acid were added to the mixture according to the procedure described in Example 1.

Upon drying, the treated mixture was viewed under a shortwave ultraviolet light having a wavelength of 254 nanometers. The sample fluoresced a red-orange color indicating the presence of rare earth minerals. The foregoing procedure results in a sensitivity to rare earth minerals of 1:10,000. (200 mg. of 10% bastnasite ore:200,000 mg. sand).

Parallel negative tests with a blank sand sample containing no bastnasite ore demonstrated that no rare earth minerals were included in the test materials.

EXAMPLE 25

Two hundred (200) milligrams of 10% bastnasite ore were mixed with a 200 gram base matrix sample of pure white washed silica sand, according to the procedure of Example 23 except that an equal volume of sodium chlorite was further mixed with the sand/bastnasite mixture instead of sodium carbonate. Two volumes of hydrochloric acid were added to the mixture according to the procedure described in Example 1.

Upon drying, the treated mixture was viewed under a shortwave ultraviolet light having a wavelength of 254 nanometers. The sample fluoresced a red-orange color indicating the presence of rare earth minerals. The foregoing procedure results in a sensitivity to rare earth minerals of 1:10,000. (200 mg. of 10% bastnasite ore:200,000 mg. sand).

Parallel negative tests with a blank sand sample containing no bastnasite ore demonstrated that no rare earth minerals were included in the test materials.

EXAMPLE 26

Two hundred (200) milligrams of 10% bastnasite ore were mixed with a 200 gram base matrix sample of pure white washed silica sand, according to the procedure of Example 23 except that an equal volume of KODAK ® "Hypo Clearing Agent" as described in Example 21 was further mixed with the sand/bastnasite mixture instead of sodium carbonate. Two volumes of hydrochloric acid were added to the mixture according to the procedure described in Example 1.

Upon drying, the treated mixture was viewed under a shortwave ultraviolet light having a wavelength of 254 nanometers. The sample fluoresced a red-orange color indicating the presence of rare earth minerals. The foregoing procedure results in a sensitivity to rare earth minerals of 1:10,000. (200 mg. of 10% bastnasite ore:200,000 mg. sand).

Parallel negative tests with a blank sand sample containing no bastnasite ore demonstrated that no rare earth minerals were included in the test materials.

EXAMPLE 27

Two hundred (200) milligrams of 10% bastnasite ore were mixed with a 200 gram base matrix sample of pure white washed silica sand, according to the procedure of Example 23 except that an equal volume of sodium hypochlorite saturated with sodium chloride as described in Example 18 was further mixed with the sand/bastnasite mixture instead of sodium carbonate. One volume of hydrochloric acid was added to the mixture according to the procedure described in Example 1.

Upon drying, the treated mixture was viewed under a shortwave ultraviolet light having a wavelength of 254 nanometers. The sample fluoresced a red-orange color indicating the presence of rare earth minerals. The foregoing procedure results in a sensitivity to rare earth minerals of 1:10,000. (200 mg. of 10% bastnasite ore:200,000 mg. sand).

Parallel negative tests with a blank sand sample containing no bastnasite ore demonstrated that no rare earth minerals were included in the test materials.

EXAMPLE 28

Two grams of 10% bastnasite ore were mixed with a 200 gram base matrix sample of pure white washed silica sand, according to the procedure of Example 23 except that an equal volume of sodium hydroxide was further mixed with the sand/bastnasite mixture instead of sodium carbonate. Two volumes of hydrochloric acid were added to the mixture according to the procedure described in Example 1.

Upon drying, the treated mixture was viewed under a shortwave ultraviolet light having a wavelength of 254 nanometers. The sample fluoresced a red-orange color indicating the presence of rare earth minerals. The foregoing procedure results in a sensitivity to rare earth minerals of 1:1,000. (2 g. of 10% bastnasite ore:200,000 mg. sand).

Parallel negative tests with a blank sand sample containing no bastnasite ore demonstrated that no rare earth minerals were included in the test materials.

EXAMPLE 29

Two grams of 10% bastnasite ore were mixed with a 200 gram base matrix sample of pure white washed silica sand, according to the procedure of Example 23 except that an equal volume of sodium bicarbonate was further mixed with the sand/bastnasite mixture instead of sodium carbonate. Two volumes of hydrochloric acid were added to the mixture according to the procedure described in Example 1.

Upon drying, the treated mixture was viewed under a shortwave ultraviolet light having a wavelength of 254 nanometers. The sample fluoresced a red-orange color indicating the presence of rare earth minerals. The foregoing procedure results in a sensitivity to rare earth minerals of 1:1,000. (2 g. of 10% bastnasite ore:200,000 mg. sand).

Parallel negative tests with a blank sand sample containing no bastnasite ore demonstrated that no rare earth minerals were included in the test materials.

Because the methods within the scope of the present invention provide varying degrees of sensitivity in detecting the presence of rare earth minerals, it is now possible to quickly test alluvial fans and "zero in" on upstream rare earth mineral deposits as the test results show higher and higher concentrations of rare earth minerals.

For example, one can now rapidly test vast areas of land for potential rare earth mineral deposits wih a very high sensitivity test. When the tests indicate the presence of rare earth minerals, it is then possible to use a less sensitive test to determine relative concentrations of rare earth minerals. The process can be repeated until the most concentrated source of rare earth minerals is located. Thus, exciting possibilities for new discoveries of rare earth minerals are now possible using the methods of the present invention.

EXAMPLE 30

Further experiments were performed to determine the optimum pH test conditions for the methods within the scope of the present invention. A quantity of 10%, 100 mesh bastnasite ore was obtained and tested for the presence of rare earth minerals. In the procedure of Examples 30, a one quarter teaspoon (¼) sample of bastnasite ore was mixed with one quarter teaspoon (¼) of a saturated aqueous solution of sodium carbonate. Thereafter, a sufficient quantity of hydrochloric acid was poured onto the mixture to give the resulting mixture a pH=1. The hydrochloric acid was technical grade hydrochloric acid purchased at a local pool supply store under the name muriatic acid. Litmus paper was used to determine the pH of the moist mixture. The mixture was thereafter allowed cool and dry.

Upon drying, the treated mixture was viewed under a shortwave ultraviolet light having a wavelength of 254 nanometers. The sample did not fluoresce a red-orange color (or any other color) indicating that a very acidic test condition (pH=1) does not produce acceptable results according to the methods within the scope of this example.

EXAMPLES 31-41

A quantity of 10%, 100 mesh bastnasite ore was obtained and tested for the presence of rare earth minerals according to the procedure of Example 30, except that sufficient hydrochloric acid was poured onto the mixture to give the resulting moist mixtures a pH from 2 to 12.

Upon drying, the treated mixtures were viewed under a shortwave ultraviolet light having a wavelength of 254 nanometers. The results of Example 30 and Examples 31-41, shown in Table I, indicate that best results are achieved if the resulting pH of the mixture prior to drying is in the range from about pH=3 to about pH=7, and preferably in the range from about pH=4 to about pH=6.

TABLE I

| Example | pH | Fluorescence observed |
| --- | --- | --- |
| 30 | 1 | no fluorescence, no ring, no matrix |
| 31 | 2 | almost no fluorescence, no ring, no matrix |
| 32 | 3 | some fluorescence, no ring, some matrix |
| 33 | 4 | better fluorescence, fair ring, good matrix |
| 34 | 5 | best fluorescence, good ring, good matrix |
| 35 | 6 | good fluorescence, best ring, good matrix |
| 36 | 7 | good fluorescence, poor ring, fair matrix |
| 37 | 8 | poor fluorescence, no ring, no matrix |
| 38 | 9 | no fluorescence, no ring, no matrix |
| 39 | 10 | no fluorescence, no ring, no matrix |
| 40 | 11 | no fluorescence, no ring, no matrix |
| 41 | 12 | no fluorescence, no ring, no matrix |

The term "ring" in Table I refers to a ring or fringe of brilliant speckling orange luminosity which develops at the leading edge of moisture penetration (on either the absorbent test receptacle or directly on the alluvial sand for in situ testing). Being orange, the "ring" lacks the red-orange tint of the fluorescence of the dried mixture discussed above. The "ring" resembles a solvent ring left on cloth when wetted with gasoline or carbon tetrachloride. The existence of a "ring" or fringe is a good indicator of rare earth content. Generally, the brighter the ring, the higher the rare earth content.

EXAMPLE 42

Further experiments were performed to determine the optimum pH test conditions for the methods within the scope of the present invention. A quantity of 10%, 100 mesh bastnasite ore was obtained and tested for the presence of rare earth minerals according to the procedure of Examples 30, except that a saturated aqueous solution of trisodium phosphate was used instead of sodium carbonate.

Upon drying, the treated mixture was viewed under a shortwave ultraviolet light having a wavelength of 254 nanometers. The sample did not fluoresce a red-orange color (or any other color) indicating that a very acidic test condition (pH=1) does not produce acceptable results according to the methods within the scope of this example.

EXAMPLES 43–53

A quantity of 10%, 100 mesh bastnasite ore was obtained and tested for the presence of rare earth minerals according to the procedures of Examples 31–41, except that a saturated solution of trisodium phosphate was used instead of sodium carbonate. Upon drying, the treated mixtures were viewed under a shortwave ultraviolet light having a wavelength of 254 nanometers. The results of Example 42 and Examples 43–53, shown in Table II, indicate that best results are achieved if the resulting pH of the mixture prior to drying is in the range from about pH=3 to about pH=7, and preferably in the range from about pH=4 to about pH=6.

TABLE II

| Example | pH | Fluorescence observed |
|---------|----|-----------------------|
| 42 | 1 | no fluorescence, no ring, no matrix |
| 43 | 2 | almost no fluorescence, no ring, no matrix |
| 44 | 3 | some fluorescence, no ring, some matrix |
| 45 | 4 | better fluorescence, fair ring, good matrix |
| 46 | 5 | best fluorescence, good ring, good matrix |
| 47 | 6 | good fluorescence, best ring, good matrix |
| 48 | 7 | good fluorescence, poor ring, fair matrix |
| 49 | 8 | poor fluorescence, no ring, no matrix |
| 50 | 9 | no fluorescence, no ring, no matrix |
| 51 | 10 | no fluorescence, no ring, no matrix |
| 52 | 11 | no fluorescence, no ring, no matrix |
| 53 | 12 | no fluorescence, no ring, no matrix |

As a consequence of Examples 30–53, when using a basic reagent solution rather than a dry, granular basic reagent, the mixture is preferably adjusted to a pH in the range from about pH=4 to about pH=6. In practice, a suitable pH is usually achieved when approximately equal volumes of acid and base are used.

It has further been found that when using all liquid reagents the pure acid is preferably applied first directly on the ore sample, allowing the ore to effervesce fully, before the basic reagent solution is applied. It has been observed that the ore itself reacts with the acid in most cases. Thus, the amount of basic reagent solution required varies according to the amount of acid which reacted with the ore sample. A useful rule of thumb when using all liquid reagents is to allow the acid-ore reaction to subside and then add the basic solution slowly until no more effervescence occurs when the base strikes the acid-ore mix.

It has also been observed when using dry, granular basic reagents that best results are achieved when one volume measure of ore sample is mixed with an approximately equal volume measure of basic reagent and thereafter acid in an amount in the range from about one (1) volume measure to about three (3) volume measures is added to the mixture.

EXAMPLES 54–65

Twelve different rare earth mineral ore samples were obtained from Shannon Minerals, Mesa, Ariz. and tested for the presence of rare earth minerals. One quarter ($\frac{1}{4}$) teaspoon of each ore sample was mixed with one quarter ($\frac{1}{4}$) teaspoon of sodium carbonate and placed in a disposable coffee filter. One half ($\frac{1}{2}$) teaspoon of hydrochloric acid was poured onto the mixture according to the procedure of Example 1. Upon drying, the treated mixture was viewed under an ultraviolet light having a wavelength of 254 nanometers and viewed for fluorescence of a red-orange color.

The chemical formula for each mineral sample tested is uncertain. Proposed chemical formulae for each mineral sample tested in Examples 54–65 are reported by Michael Fleischer, *Glossary of Mineral Species* 1983, The Mineralogical Record, Inc. (hereinafter referred to as "F"), by Orosino C. Smith, *Identification and Quantitative Chemical Analysis of Minerals*, second edition D. Van Nostrand Co., New York, 1954 (hereinafter referred to as "S"), and by John W. Adams, *Bibliography of the Geology and Mineralogy of the Rare Earths and Scandium to* 1971 (hereinafter referred to as "A"). The results of Examples 54–65 are shown below.

EXAMPLE 54

Allanite Y

No location of the source for the Allanite Y tested was provided. The chemical formulae for Allanite Y are as follows:
F: $(Y,Ce,Ca)_2(Al,Fe^{+3})_3(SiO_4)OH$
S: $4(Ca,Fe)O.3(Al,Ce,Fe,Di)_2O_3.6SiO_2.H_2O$
A: none given A good, confined red-orange fluorescence was observed. There was small fringing and good matrix fluorescence.

EXAMPLE 55

Allanite

The sample of Allanite tested was found in Canada. The chemical formulae for Allanite are as follows:
F: $(Ce,Ca,Y)_2(Al,Fe^{+3})_3(SiO_4)OH$
S: $4(Ca,Fe)O.3(Al,Ce,Fe,Di)_2O_3.6SiO_2.H_2O$
A: $(Ca,Ce,Th)_2(Al,Fe,Mg)_3Si_3O_{12}(OH)$ A poor, deep red fluorescence with some orange was observed. There also was a large, deep red, diffused fringe observed. The matrix was almost purple.

EXAMPLE 56

Bastnasite

The sample of Bastnasite tested was found in Lincoln County, N. Mex. The chemical formulae for Bastnaesite are as follows:
F: $(Ce,La)(CO_3)F$
S: $(Ce,La,Di)F.CO_2$
A: $(Ce,La)FCO_3$ A bright orange fluorescence was observed. There was a good fringe and a good matrix.

EXAMPLE 57

Davidite

The sample of Davidite tested was found in Australia. The chemical formulae for Davidite are as follows:
F: $(La,Ce)(Y,U,Fe^{+2})(Ti,Fe^{+3})_{20}(O,OH)_{38}$
S: none given
A: $(Fe^{+2},La,U,Ca)_6(Ti,Fe^{+3})_{13}(O,OH)_{36}$ Fair, spotty, red-orange fluorescence was observed. There was a dispersed, but discernable, fringe and fair matrix fluorescence.

EXAMPLE 58

Euxenite

The sample of Euxenite tested was found in Wyoming. The chemical formulae for Euxenite are as follows:
F: $(Y,Ca,Ce,U,Th)(Nb,Ta,Ti)_2O_6$
S: none given
A: none given
Good, red-orange fluorescence was observed. There was a good halo and a fair matrix fluorescence.

EXAMPLE 59

Euxenite-Y

The sample of Euxenite-Y tested was found in Arizona. The chemical formulae for Euxenite-Y are as follows:
F: none given
S: $(Y,Ca,Ce,U,Th)(Nb,Ta,Ti)_2O_6$
A: none given
Good, solid, red-orange fluorescence was observed. There was no halo or fringe, but good matrix fluorescence was observed.

EXAMPLE 60

Fergusonite

The sample of Fergusonite tested was found in Canada. The chemical formulae for Fergusonite are as follows:
F: $YNbO_4$
S: $(Y,Er,Ce,Fe)(Ta,Nb,Ti)O_4$
A: $(Y,Er,Ce,Fe)(Nb,Ta,Ti)O_4$
Bright green spots in addition to the usual red-orange fluorescence was observed. There was a minor red halo and fringe and fair matrix fluorescence.

Due to the unusual bright green spots observed, a second sample of Fergusonite was obtained from Shannon Minerals and tested for the presence of rare earth minerals according to the procedure of Example 60. The second Fergusonite sample did not fluoresce green.

Thereafter, quantities of both Fergusonite samples were analyzed by Reed Engineering, Assayers and Refiners, Costa Mesa, Calif. The Fergusonite sample which fluoresced green possessed quantities of magnesium, niobium, potassium, strontium, zirconium, and erbium not found in the other Fergusonite sample. Of these elements, it is presently believed either niobium, zirconium, or erbium caused the bright green fluorescence.

It is also currently believed that the original Fergusonite sample may have actually been Formanite or a mixture of Formanite and Fergusonite due to the common inclusion of thorium and yttrium in the chemical analysis. Moreover, it is known that Fergusonite and Formanite are closely related minerals such that a "Fergusonite-Formanite Series" exists. See Adms, *Bibliography of the Geology and Mineralogy of the Rare Earths and Scandium to* 1971, page IX.

EXAMPLE 61

Parisite

The sample of Parisite tested was found in Montana. The chemical formulae for Parisite are as follows:
F: $(Ce,La)_2Ca(CO_3)_3F_2$
S: $2(Ce,La,Di,Th)OF.CaO.3CO_3$
A: $(Ce,La)_2Ca(CO_3)_3F_2$
A deep purple color was observed, although no true fluorescence was observed. There was a deep black purple fringe, and no halo or red matrix were observed.

Due to the unexpected abscence of red-orange fluorescence, a quantity of the same parasite sample tested in Example 61 was further analyzed by Reed Engineering, Assayers and Refiners, Costa Mesa, Calif. The alleged parasite sample was assayed to contain no rare earth minerals. Thus, the ore sample tested in Example 61 was not a true parasite sample.

EXAMPLE 62

Polymignite

The sample of Polymignite tested was found in Norway. The chemical formulae for Polymignite are as follows:
F: $(Ca,Fe,Y,Th)(Nb,Ti,Ta,Zr)O_4$
S: $(Ca,Fe,Y,Etc,Zr,Th)(Nb,Ti,Ta)O$
A: $(Ca,Fe,Ce)(Zr,Ti,Nb,Ta)_2O_6$
The term "Etc" found in Orsino L. Smith's formula above is believed to represent the series usually found after Y in the rare earth series, e.g., La, Ce, Pr, Nd, Pm. Bright spots of orange fluorescence were observed. There was no fringe or matrix observed.

EXAMPLE 63

Cheralite

The sample of Cheralite tested was found in Wyoming. The chemical formulae for Cheralite are as follows:
F: $(Ca,Ce,Th)(P,Si)O_4$
S: not listed
A: $(Ca,Ce,Th)(P,Si)O_4$
Very bright red-orange fluorescence was observed. There was a good halo and fringe, and good matrix fluorescence was observed.

EXAMPLE 64

Samarskite

The sample of Samarskite tested was found in Maine. The chemical formulae for Samarskite are as follows:
F: $(Y,Ce,U,Ca,Pb)(Nb,Ta,Ti,Sn)_2O_6$
S: $(Y,Er,Ce,U,Ca,Fe,Pb,Th)(Nb,Ta,Ti,Sn)_2O_6$
A: $(Y,Fe,U)(Nb,Ti,Ta)(O,OH)_6$
Slight red-orange fluorescence was observed. There was a slight fringe or halo, and good matrix fluorescence was observed.

EXAMPLE 65

Evans-Lou Pegmatite

The test sample of Evans-Lou Pegmatite used was found in Canada. A proposed chemical formula for Evans-Lou Pegmatite is found in *The Mineralogical Record*, March-April 1972, page 74 which is incorporated herein by specific reference. A fair, red-orange fluorescence with good dispersement was observed. There was a slight fringe, and good matrix fluorescence was observed.

As a result of Examples 54–65, it will be appreciated that the methods within the scope of the present invention have broad applicability to a wide variety of rare earth minerals found throughout the world. The above methods are quick, inexpensive, very specific, and quite dramatic in results. The equipment and chemicals needed are inexpensive, easy to carry and relatively safe.

EXAMPLE 66

An in situ test was performed at a location downstream from the mine at Mountain Pass, Calif. A shallow furrow about one inch deep and about two feet long was scratched into the alluvial sand. In the first third of the furrow, one half (½) teaspoon of dry, granular KODAK ® "Hypo Clearing Agent," described in Example 21, was mixed with the alluvial sand. In the middle third two tablespoons of a 1:6 aqueous solution of the KODAK ® "Hypo Clearing Agent" was applied to the sand. In the remaining third two tablespoons of a 10% aqueous solution of sodium hypochlorite saturated with ordinary table salt, described in Example 18, was applied to the sand.

Six tablespoons of hydrochloric acid, described in Example 18, were applied evenly along the entire two feet of the furrow bottom and allowed to effervesce and dry overnight. The following day, after dark, the furrow was examined under a shortwave ultraviolet light described in Example 18. Those portions of the furrow treated with the aqueous "Hypo Clearing Agent" and with the sodium hypochlorite solution exhibited a strong red-orange fluorescence. Whereas, the portion of the furrow treated with the dry "Hypo Clearing Agent" was dark and non-responsive. It is believed the acid overwhelmed the base creating a hygroscopic condition which would not dry out.

EXAMPLE 67

An in situ test was performed at approximately the same location and in the same manner as in Example 65, except that three furrows were formed and tested with 1:6 aqueous solutions of sodium hydroxide, sodium carbonate, trisodium phosphate, sodium sulfite, KODAK ® "Hypo Clearing Agent", and a 10% solution of sodium hypochlorite saturated with sodium chloride. The basic reagents used are described in Examples 1, 2, 3, 21, 21, and 18 respectively.

One half of each furrow was treated with very dilute hydrochloric acid (one part hydrochloric acid to 15 parts water) and the remainder of each furrow was treated with undiluted hydrochloric acid. Those furrow portions treated with the undiluted hydrochloric acid effervesced strongly and fluoresced a bright red-orange color. Those portions treated with the diluted hydrochloric acid produced in almost negative results.

From the results of Examples 66 and 67, it is presently preferred to use hydrochloric acid that is not diluted very much, if at all. Whereas, adding water to the base solution does not appear to diminish the intensity of the fluorescence so long as the sample is allowed to dry thoroughly. It is presently believed that too much undiluted acid can overwhelm the base, but copious amounts of diluted base does not overwhelm the acid as long as drying can occur.

EXAMPLE 68

A quantity of bastnasite ore was obtained from the mine at Mountain Pass, Calif. and tested for the presence of rare earth minerals according to the procedure of Example 1, except that ACTIVATE, a swimming pool product manufactured by Great Lakes Biochemical Co., Inc., Milwaukee, Wis. was mixed with the bastnasite ore instead of the sodium hydroxide. The ACTIVATE product contains 32.18% potassium peroxymonosulfate as its active ingredient (67.82% inert ingredients).

Upon drying, the treated mixture was viewed under a shortwave ultraviolet light having a wavelength of 254 nanometers. The sample fluoresced a bright red-orange color indicating that the basic reagent potassium peroxymonsulfate produces acceptable results according to the procedures of the present invention.

EXAMPLE 69

A quantity of bastnasite ore was obtained from the mine at Mountain Pass, Calif. and tested for the presence of rare earth minerals. The bastnasite ore was coarse, having a particle sizes less than one quarter (¼) inch. The bastnasite ore was unmortared, unsifted mill run ore believed to contain a rare earth mineral content of six percent (6%) according to the mine manager.

According to the procedure of Example 69, one quarter (¼) teaspoon of the bastnasite ore was mixed with one quarter (¼) teaspoon of ACTIVATE, a swimming pool product manufactured by Great Lakes Biochemical Co., Inc., Milwaukee, Wis. The ACTIVATE product contains 32.18% potassium peroxymonosulfate as its active ingredient and 67.82% inert ingredients. The mixture of bastnasite ore and potassium peroxymonosulfate was placed in a disposable coffee filter.

One quarter (¼) teaspoon of ENHANCE, a bromine containing swimming pool product manufactured by Great Lakes Biochemical Co., Inc., Milwaukee, Wis. The ENHANCE product contains 32.18% sodium bromide and 67.82% inert ingredients. The sodium bromide solution was gradually poured onto the mixture.

The mixture was thereafter allowed to dry. Upon drying, the mixture was viewed under a shortwave ultraviolet light having a wavelength of 254 nanometers. The sample fluoresced a red-orange color indicating the presence of rare earth minerals. The fluorescence had an intensity about the same as that produced by the procedure of Example 1.

EXAMPLE 70

A quantity of bastnasite ore was obtained from the mine at Mountain Pass, Calif. and tested for the presence of rare earth minerals according to the procedure of Example 18, except that a BIOGARD ® solution was used instead of aqueous sodium hypochlorite. The BIOGARD ®, manufactured by BIO-LAB Inc., Decatur, Ga., is composed of sodium dichloro-S-triazinetrione (81.6%), sodium bromide (14.6%), and inert ingredients (3.8%).

Upon drying, the treated mixture was viewed under a shortwave ultraviolet light having a wavelength of 254 nanometers. The sample fluoresced a bright red-orange color indicating the presence of rare earth minerals. The fluorescence was markedly more intense, with a good matrix and ring, than with pure sodium dichloro-S-triazinetrione. See Example 22 using "Leslies's Chlorbrite." Evidently the sodium bromide enhances the activity of the dichloro-S-triazinetrione.

SUMMARY

From the foregoing, it will be appreciated that the present invention provides methods for detecting rare earth minerals which can be carried out directly in the field. This is a significant improvement over existing methods for detecting rare earth minerals which must be performed in the laboratory.

Additionally the present invention provides methods for detecting rare earth minerals which provide quick and accurate results which are easy to interpret, reproducible, stable, easily recorded, and storable. Moreover, the methods within the scope of the present invention enable a prospector to test an ore sample and accurately determine in a matter of minutes whether rare earth minerals are present.

Likewise, the present invention provides methods for detecting rare earth minerals which do not require sophisticated chemicals, processes, or equipment. The present invention uses simple and easily obtained reagents which are relatively safe and self neutralizing.

It will also be appreciated that the present invention provides methods for detecting rare earth minerals which do not require radioactivity detectors, thereby avoiding the expense, nuisance, and regulatory safeguards associated with radioactivity detectors.

Finally, the present invention provides methods for detecting rare earth minerals which provide accurate semiquantitative results, thereby permitting the user to "zero in" on new and exiting rare earth mineral discoveries.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by U.S. Letters Patent is:

1. A method for detecting rare earth minerals in the field comprising the steps of:
   (a) obtaining an ore sample to be tested for the presence of rare earth minerals;
   (b) mixing the ore sample with a basic reagent to form a mixture;
   (c) treating the mixture with a halide acid;
   (d) allowing the mixture to react and dry; and
   (e) examining the ore sample under a shortwave ultraviolet light for fluorescence of a red-orange color.

2. A method for detecting rare earth minerals in the field as defined in claim 1, wherein the ore sample contains ore granules up to about one quarter (¼) inch in diameter.

3. A method for detecting rare earth minerals in the field as defined in claim 1, wherein the basic reagent comprises an alkali metal hydroxide.

4. A method for detecting rare earth minerals in the field as defined in claim 3, wherein the alkali metal hydroxide comprises sodium hydroxide.

5. A method for detecting rare earth minerals in the field as defined in claim 1, wherein the basic reagent comprises an alkali metal carbonate.

6. A method for detecting rare earth minerals in the field as defined in claim 5, wherein the alkali metal carbonate comprises sodium carbonate.

7. A method for detecting rare earth minerals in the field as defined in claim 1, wherein the basic reagent comprises trisodium phosphate.

8. A method for detecting rare earth minerals in the field as defined in claim 1, wherein the basic reagent comprises sodium dichloro-S-triazinetrione.

9. A method for detecting rare earth minerals in the field as defined in claim 1, wherein the basic reagent comprises sodium chlorite.

10. A method for detecting rare earth minerals in the field as defined in claim 1, wherein the basic reagent comprises sodium sulfite.

11. A method for detecting rare earth minerals in the field as defined in claim 1, wherein the basic reagent comprises sodium bicarbonate.

12. A method for detecting rare earth minerals in the field as defined in claim 1, wherein the basic reagent comprises sodium hypochlorite.

13. A method for detecting rare earth minerals in the field as defined in claim 1, wherein the basic reagent comprises an aqueous basic solution.

14. A method for detecting rare earth minerals in the field as defined in claim 13, wherein the basic reagent comprises an aqueous solution of sodium hypochlorite having a concentration in the range from about 5% to about 15%.

15. A method for detecting rare earth minerals in the field as defined in claim 14, wherein the sodium hypochlorite solution further comprises sodium chloride.

16. A method for detecting rare earth minerals in the field as defined in claim 1, wherein the halide acid comprises hydrochloric acid.

17. A method for detecting rare earth minerals in the field as defined in claim 1, wherein the ore sample is examined under a shortwave ultraviolet light having a wavelength of about 254 nanometers.

18. A method for detecting rare earth minerals in the field as defined in claim 1, wherein the volume of ore sample obtained is in the range from about one quarter (¼) to about two tablespoons.

19. A method for detecting rare earth minerals in the field comprising the steps of:
   (a) obtaining an ore sample to be tested for the presence of rare earth minerals;
   (b) mixing one volume measure of the ore sample with an approximately equal volume measure of basic reagent to form a mixture;
   (c) treating the mixture with a quantity of a halide acid in the range from about one volume measure to about three volume measures;
   (d) allowing the mixture to react, cool off, and dry; and
   (e) examining the ore sample under a shortwave ultraviolet light for fluorescence of a red-orange color.

20. A method for detecting rare earth minerals in the field as defined in claim 19, wherein the basic reagent comprises an alkali metal carbonate.

21. A method for detecting rare earth minerals in the field as defined in claim 20, wherein the alkali metal carbonate comprises sodium carbonate.

22. A method for detecting rare earth minerals in the field as defined in claim 19, wherein the basic reagent comprises trisodium phosphate.

23. A method for detecting rare earth minerals in the field as defined in claim 19, wherein the basic reagent comprises sodium dichloro-S-triazinetrione.

24. A method for detecting rare earth minerals in the field as defined in claim 19, wherein the basic reagent comprises sodium chlorite.

25. A method for detecting rare earth minerals in the field as defined in claim 19, wherein the basic reagent comprises sodium sulfite.

26. A method for detecting rare earth minerals in the field as defined in claim 19, wherein the basic reagent comprises sodium bicarbonate.

27. A method for detecting rare earth minerals in the field as defined in claim 19, wherein the basic reagent comprises sodium hypochlorite.

28. A method for detecting rare earth minerals in the field as defined in claim 19, wherein the basic reagent comprises an aqueous basic solution.

29. A method for detecting rare earth minerals in the field as defined in claim 28, wherein the basic reagent comprises an aqueous solution of sodium hypochlorite having a concentration in the range from about 5% to about 15%.

30. A method for detecting rare earth minerals in the field as defined in claim 29, wherein the sodium hypochlorite solution further comprises sodium chloride.

31. A method for detecting rare earth minerals in the field as defined in claim 19, wherein the halide acid comprises hydrochloric acid.

32. A method for detecting rare earth minerals in the field as defined in claim 19, wherein the ore sample is examined under a shortwave ultraviolet light having a wavelength of about 254 nanometers.

33. A method for detecting rare earth minerals in the field as defined in claim 19, wherein the basic reagent comprises an alkali metal hydroxide.

34. A method for detecting rare earth minerals in the field as defined in claim 33, wherein the alkali metal hydroxide comprises sodium hydroxide.

35. A method for detecting rare earth minerals comprising the steps of:
(a) treating an ore sample to be tested for the presence of rare earth minerals with approximately equal volume measures of an aqueous basic reagent solution and a halide acid;
(b) allowing the ore sample to react, cool off, and dry; and
(c) examining the ore sample under a shortwave ultraviolet light for fluorescence of a red-orange color indicating the presence of rare earth minerals.

36. A method for detecting rare earth minerals in the field as defined in claim 35, wherein the halide acid comprises hydrochloric acid.

37. A method for detecting rare earth minerals in the field as defined in claim 35, wherein the basic reagent aqueous solution comprises an alkali metal hydroxide.

38. A method for detecting rare earth minerals in the field as defined in claim 37, wherein the alkali metal hydroxide comprises sodium hydroxide.

39. A method for detecting rare earth minerals in the field as defined in claim 35, wherein the basic reagent aqueous solution comprises an alkali metal carbonate.

40. A method for detecting rare earth minerals in the field as defined in claim 35, wherein the alkali metal carbonate comprises sodium carbonate.

41. A method for detecting rare earth minerals in the field as defined in claim 35, wherein the basic reagent aqueous solution comprises trisodium phosphate.

42. A method for detecting rare earth minerals in the field as defined in claim 35, wherein the basic reagent aqueous solution comprises sodium dichloro-S-triazinetrione.

43. A method for detecting rare earth minerals in the field as defined in claim 35, wherein the basic reagent aqueous solution comprises sodium chlorite.

44. A method for detecting rare earth minerals in the field as defined in claim 35, wherein the basic reagent aqueous solution comprises sodium sulfite.

45. A method for detecting rare earth minerals in the field as defined in claim 35, wherein the basic reagent aqueous solution comprises sodium bicarbonate.

46. A method for detecting rare earth minerals in the field as defined in claim 35, wherein the quantity of aqueous basic reagent solution and the quantity of halide acid which treat the ore sample result in a pH in the range from about pH=3 to about pH=7.

47. A method for detecting rare earth minerals in the field as defined in claim 46, wherein the resulting pH is in the range from about pH=4 to about pH=6.

48. A method for detecting rare earth minerals in the field as defined in claim 35, wherein the aqueous basic reagent solution comprises an aqueous solution of sodium hypochlorite having a concentration in the range from about 5% to about 15%.

49. A method for detecting rare earth minerals in the field as defined in claim 35, wherein the sodium hypochlorite solution further comprises sodium chloride.

50. A method for detecting rare earth minerals comprising the steps of:
(a) obtaining an ore sample to be tested for the presence of rare earth minerals;
(b) treating the ore sample with a quantity of aqueous basic reagent solution and a quantity of halide acid, such that the resulting mixture has a pH in the range from about pH=3 to about pH=7;
(c) allowing the ore sample to react and dry; and
(d) examining the ore sample under a shortwave ultraviolet light for fluorescence of a red-orange color indicating the presence of rare earth minerals.

51. A method for detecting rare earth minerals in the field as defined in claim 50, wherein the resulting pH is in the range from about pH=4 to about pH=6.

* * * * *

UNITED STATES PATENT AND TRADEMARK OFFICE
CERTIFICATE OF CORRECTION

PATENT NO. : 4,876,206

DATED : October 24, 1989

INVENTOR(S) : Wayne L. Sayer

It is certified that error appears in the above-identified patent and that said Letters Patent is hereby corrected as shown below:

Column 5, line 62, delete "used"
Column 8, line 20, "having a particle sizes" should be --having a particle size--
Column 11, line 1, "showed a good a" should be --showed a good --
Column 11, line 55, "having a particle sizes" should be --having a particle size--
Column 12, line 24, "having a particle sizes" should be --having a particle size--
Column 12, line 49, "having a particle sizes" should be --having a particle size--
Column 22, line 14, "having a particle sizes" should be --having a particle size--

Signed and Sealed this

Nineteenth Day of February, 1991

Attest:

HARRY F. MANBECK, JR.

*Attesting Officer*      *Commissioner of Patents and Trademarks*